United States Patent
Oishi et al.

(10) Patent No.: US 7,096,717 B2
(45) Date of Patent: Aug. 29, 2006

(54) CONTROL DEVICE OF GAS SENSOR

(75) Inventors: Hidetoshi Oishi, Wako (JP); Hirotoshi Inoue, Wako (JP); Takashi Sasaki, Wako (JP); Takashi Saito, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 62 days.

(21) Appl. No.: 10/938,297

(22) Filed: Sep. 10, 2004

(65) Prior Publication Data
US 2005/0072212 A1     Apr. 7, 2005

(51) Int. Cl.
*G01N 25/00*     (2006.01)
(52) U.S. Cl. ............... 73/25.01; 73/23.2; 73/23.21; 73/25.05; 73/31.05
(58) Field of Classification Search ........... 73/23.2, 73/23.31, 25.01, 25.04, 25.05, 31.05, 23.21
See application file for complete search history.

(56) References Cited

U.S. PATENT DOCUMENTS 4,045,177 A * 8/1977 McNally ............... 422/96
4,063,447 A * 12/1977 Mathison ............... 73/23.4
4,951,507 A * 8/1990 Takahashi et al. ............ 73/497

FOREIGN PATENT DOCUMENTS

JP     A-6-223850     8/1994

\* cited by examiner

*Primary Examiner*—Daniel S. Larkin
(74) *Attorney, Agent, or Firm*—Hamre, Schumann, Mueller & Larson, P.C.

(57) ABSTRACT

When the ignition switch of a vehicle is turned OFF, a purging process for increasing the flow of an off-gas fluidizing in each of the outlet side pipings of a fuel cell and discharging water remaining in a fuel cell system to an outside is started to be executed, and the amount of current conductance to the heater of the gas sensor is increased synchronously with the start of the execution of the purging process. With the completion of the purging process, the fluidization of the off-gas in each of the outlet side pipings stops, and the amount of current conductance to each of the units of the gas sensor (for example, an electrifying voltage) is gradually decreased depending on a predetermined current conductance reducing amount which is preset, thereby stopping the current conductance to each of the units and the amount of current conductance to the heater is gradually decreased, thereby stopping the current conductance to the heater.

8 Claims, 6 Drawing Sheets

CONTROL DEVICE OF GAS SENSOR

This application claims foreign priority based on Japanese Patent application No. 2003-328924, filed September, 2003, the contents of which is incorporated herein by reference in its entirety.

BACKGROUND OF THE INVENTION

1. Field of the Invention

The present invention relates to a control device of a gas sensor, such as a contact combustion type hydrogen sensor, to be mounted on a fuel cell vehicle.

2. Description of the Related Art

For example, in the related arts, a solid polymer electrolyte fuel cell comprises a stack (hereinafter referred to as a fuel cell) which is constituted by laminating a plurality of cells on a cell formed by interposing a solid polymer electrolyte membrane between a fuel electrode and an oxygen electrode from both sides. Hydrogen is supplied as a fuel to the fuel electrode and air is supplied as an oxidizing agent to the oxygen electrode, and a hydrogen ion generated by a catalytic reaction at the fuel electrode passes through the solid polymer electrolyte membrane and moves to the oxygen electrode, and causes an electrochemical reaction to oxygen at the oxygen electrode, thereby generating a power.

Referring to a fuel cell, such as the solid polymer electrolyte fuel cell, there has conventionally been known a protecting device comprising a hydrogen detector (a gas sensor) in a discharge system on an oxygen electrode side of the fuel cell and serving to block the supply of a fuel when detecting that hydrogen on a fuel electrode side leaks toward the oxygen electrode side through a solid polymer electrolyte membrane by means of the hydrogen detector, such as disclosed in JP-A-6-223850.

Referring to the hydrogen detector, moreover, there has been known a hydrogen detector of a gas contact combustion type which comprises a pair of a gas detecting unit formed of a catalyst, such as platinum, and a temperature compensating unit and serves to detect the concentration of a hydrogen gas depending on a difference in an electrical resistance generated together with the temperature compensating unit set in a relatively low temperature state, such as an atmospheric temperature, when the gas detecting unit is brought into a relatively high temperature state by heat generated through a combustion in the contact of hydrogen with the catalyst, such as platinum.

In the hydrogen detector of a gas contact combustion type, for example, the temperature of each unit drops suddenly due to the stop of current conductance when the actuation stops, for example. In such a case, there is a possibility that a dew condensation might be generated on the surface of each unit in case of the temperature drop of the unit becoming equal to or lower than the dew-point temperature of an atmosphere.

Furthermore, in the fuel cell such as the solid polymer electrolyte fuel cell, described above, water (humidifying water) is mixed with a reaction gas supplied to the fuel cell (for example, hydrogen or air) by means of a humidifier in order to maintain the ion conductance of the solid polymer electrolyte membrane, and furthermore, reaction product water is generated by an electrochemical reaction during the operation of the fuel cell. For this reason, an exhaust gas of the fuel cell, particularly, an exhaust gas on an oxygen electrode side has a high wettability.

In the protecting device of the fuel cell according to an example of the conventional art, therefore, a dew condensation is generated on a hydrogen detector provided in the passage for an off-gas having a high wettability which is discharged from the fuel cell due to the off-gas in some cases. In these cases, there is a possibility that the hydrogen detector might be deteriorated or broken. In the solid polymer electrolyte fuel cell as described above, particularly, an ordinary operating temperature is lower than the vaporization temperature of water and the off-gas is changed into a gas having a large amount of moisture with a high humidity and is thus discharged. For this reason, there is a problem in that the moisture in the off-gas is apt to be condensed. In the case in which the hydrogen detector of a gas contact combustion type is particularly provided in a discharge system on the oxygen electrode side of the fuel cell, there is a possibility that a local temperature distribution might be unevenly generated over the surface of the unit, resulting in the breakage of the unit or a reduction in a sensitivity if the operation of a gas sensor stops and the current conductance is carried out in next starting in a state in which the humidifying water or the reaction product water is stuck onto a gas detecting unit.

SUMMARY OF THE INVENTION

The invention has been made in consideration of the circumstances and has an object to provide a control device of a gas sensor which can prevent the breakage, deterioration and a reduction in precision in detection of a gas sensor.

In order to solve the problems and to attain the object, a first aspect of the invention is directed to a control device of a gas sensor for detecting a concentration of a detected gas contained in a gas to be inspected based on a difference in an electrical resistance value between a detecting unit (for example, a detecting unit 31 according to an embodiment which will be described below) and a compensating unit (for example, a temperature compensating unit 32 according to the embodiment which will be described below), comprising unit current conductance stopping means (for example, steps S01 and S24 in the embodiment which will be described below) for gradually decreasing amounts of current conductance to the detecting unit and the compensating unit.

According to the control device of a gas sensor having the structure described above, the amounts of current conductance to the detecting unit and the compensating unit are gradually decreased by the unit current conductance stopping means when the operation of the gas sensor stops. Consequently, it is possible to prevent the surface temperature of each unit from being suddenly dropped to be a temperature which is equal to or lower than the dew-point temperature of a gas to be inspected, and to prevent a dew condensation from being generated on the surface of each unit.

Furthermore, a second aspect of the invention is directed to the control device of a gas sensor, wherein the detecting unit and the compensating unit are provided in a gas detecting chamber (for example, a gas detecting chamber 27 according to the embodiment which will be described below) for introducing the gas to be inspected, the control device further comprising a heater provided in the gas detecting chamber, and heater current conductance stopping means (for example, steps S02 and S25 according to the embodiment which will be described below) for gradually decreasing an amount of current conductance to the heater.

According to the control device of a gas sensor having the structure described above, the amounts of current conductance to the detecting unit and the compensating unit are gradually decreased by the unit current conductance stopping means, and furthermore, the amount of current conductance to the heater is gradually decreased by the heater current conductance stopping means. Consequently, it is possible to prevent the surface temperature of each unit and the temperature of the atmosphere in the gas detecting chamber from being suddenly dropped to be temperatures which are equal to or lower than the dew-point temperature of the atmosphere.

Moreover, a third aspect of the invention is directed to the control device of a gas sensor, further comprising state detecting means (for example, a sensor 37 according to the embodiment which will be described below) for detecting a humidity state of an atmosphere in the gas detecting chamber, the heater current conductance stopping means decreasing the amount of current conductance to the heater depending on the humidity state of the atmosphere in the gas detecting chamber which is detected by the state detecting means.

According to the control device of a gas sensor having the structure described above, the amount of current conductance to the heater is decreased depending on the humidity state of the atmosphere in the gas detecting chamber. Consequently, it is possible to properly reduce the amount of current conductance to the heater while preventing the surface temperature of each unit and the temperature of the atmosphere in the gas detecting chamber from being dropped to be temperatures which are equal to or lower than the dew-point temperature of the atmosphere.

Furthermore, a fourth aspect of the invention is directed to the control device of a gas sensor, wherein the detecting unit and the compensating unit are provided in a gas detecting chamber (for example, the gas detecting chamber 27 according to the embodiment which will be described below) for introducing the gas to be inspected, the control device further comprising state detecting means (for example, the sensor 37 according to the embodiment which will be described below) for detecting a humidity state of an atmosphere in the gas detecting chamber, the unit current conductance stopping means decreasing the amounts of current conductance to the detecting unit and the compensating unit depending on the humidity state of the atmosphere in the gas detecting chamber which is detected by the state detecting means.

According to the control device of a gas sensor having the structure described above, the amounts of current conductance to the detecting unit and the compensating unit are decreased depending on the humidity state of the atmosphere in the gas detecting chamber. Consequently, it is possible to properly reduce the amount of current conductance to each unit while preventing the surface temperature of the unit and the temperature of the atmosphere in the gas detecting chamber from being dropped to be temperatures which are equal to or lower than the dew-point temperature of the atmosphere.

Moreover, a fifth aspect of the invention is directed to the control device of a gas sensor, wherein the detecting unit and the compensating unit are provided in a gas detecting chamber (for example, the gas detecting chamber 27 according to the embodiment which will be described below) for introducing the gas to be inspected, and the unit current conductance stopping means sets the amounts of current conductance to the detecting unit and the compensating unit in such a manner that surface temperatures of the detecting unit and the compensating unit are higher than a dew-point temperature of an atmosphere in the gas detecting chamber.

According to the control device of a gas sensor having the structure described above, it is possible to properly reduce the amount of current conductance to each unit while preventing that a dew condensation is generated on the surfaces of the detecting unit and the compensating unit.

Furthermore, a sixth aspect of the invention is directed to the control device of a gas sensor, wherein the heater current conductance stopping means sets the amount of current conductance to the heater in such a manner that surface temperatures of the detecting unit and the compensating unit are higher than a dew-point temperature of an atmosphere in the gas detecting chamber.

According to the control device of a gas sensor having the structure described above, it is possible to properly reduce the amount of current conductance to the heater while preventing that a dew condensation is generated on the surfaces of the detecting unit and the compensating unit.

According to the control device of a gas sensor in accordance with the first aspect of the invention, it is possible to prevent the surface temperature of each unit from being suddenly dropped to a temperature which is equal to or lower than the dew-point temperature of a gas to be inspected, and to prevent a dew condensation from being generated on the surface of each unit.

According to the control device of a gas sensor in accordance with the second aspect of the invention, furthermore, it is possible to prevent the surface temperature of each unit and the temperature of the atmosphere in the gas detecting chamber from being suddenly dropped to temperatures which are equal to or lower than the dew-point temperature of the atmosphere.

According to the control device of a gas sensor in accordance with the third aspect of the invention, moreover, it is possible to properly reduce the amount of current conductance to the heater while preventing the surface temperature of each unit and the temperature of the atmosphere in the gas detecting chamber from being dropped to temperatures which are equal to or lower than the dew-point temperature of the atmosphere.

According to the control device of a gas sensor in accordance with the fourth aspect of the invention, furthermore, it is possible to properly reduce the amount of current conductance to each unit while preventing the surface temperature of the unit and the temperature of the atmosphere in the gas detecting chamber from being dropped to temperatures which are equal to or lower than the dew-point temperature of the atmosphere.

According to the control device of a gas sensor in accordance with the fifth aspect of the invention, moreover, it is possible to properly reduce the amount of current conductance to each unit while preventing that a dew condensation is generated on the surfaces of the detecting unit and the compensating unit.

According to the control device of a gas sensor in accordance with the sixth aspect of the invention, furthermore, it is possible to properly reduce the amount of current conductance to the heater while preventing that a dew condensation is generated on the surfaces of the detecting unit and the compensating unit.

DESCRIPTION OF THE PREFERRED EMBODIMENTS

A control device of a gas sensor according to an embodiment of the invention will be described below with reference to the accompanying drawings.

Figure 1:
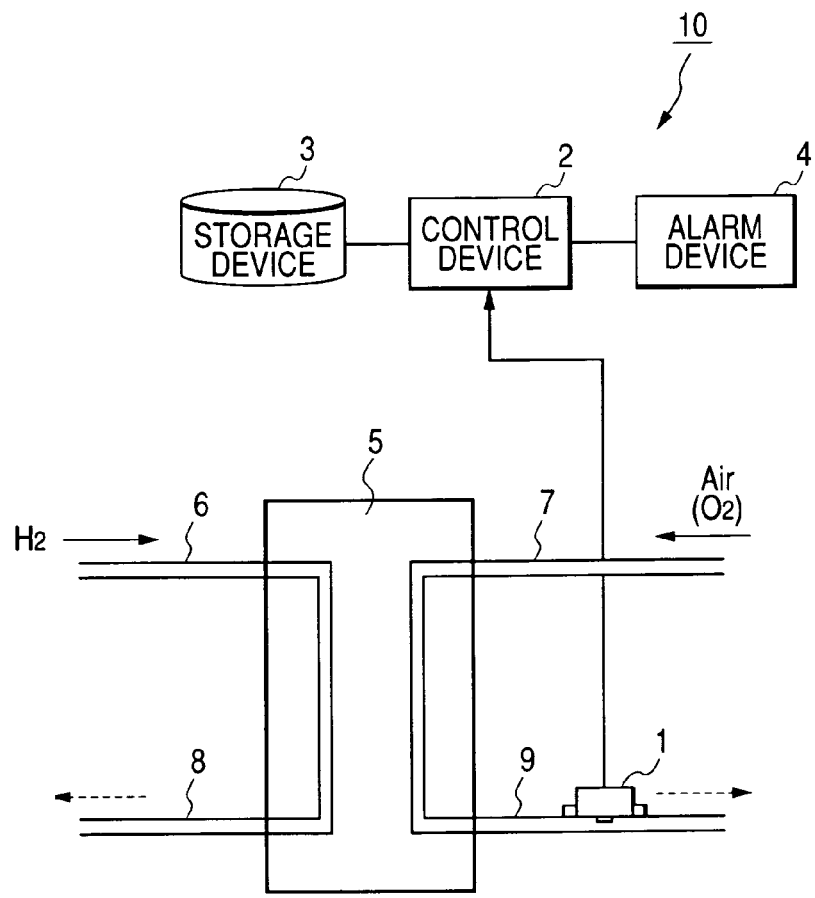
FIG. 1 is a diagram showing the structure of the main part of a fuel cell system comprising a gas sensor according to an embodiment of the invention.

A gas sensor 1 according to the embodiment constitutes a hydrogen sensor for detecting hydrogen, for example, and is provided on an outlet side piping 9 at an oxygen electrode side and serves to confirm that the hydrogen is not discharged from the outlet side piping 9 in a fuel cell system 10 comprising a control device 2, a storage device 3, an alarm device 4, a fuel cell 5 to be the power source of a vehicle, and pipings 6, 7, 8 and 9 connected to the fuel cell 5 and serving to supply a reaction gas as shown in FIG. 1, for example.

The control device 2 is connected to the gas sensor 1 attached to the outlet side piping 9 on the oxygen electrode side and decides whether or not the abnormal state of the fuel cell 5 is generated according to the result of a comparison between a detection signal output from the gas sensor 1 and a predetermined decision threshold stored in the storage device 3, and outputs an alarm through the alarm device 4 when deciding that the abnormal state is set, for example. The storage device 3 stores the map of a predetermined decision threshold for the detected value of the gas sensor 1 corresponding to the operation state of the fuel cell 5, for example, a differential pressure between electrodes or an operating pressure.

The fuel cell 5 is mounted on a vehicle as the power source of an electric vehicle, for example, and a membrane electrode assembly interposing a solid polymer electrolyte membrane formed by a cation exchange membrane between a fuel electrode and an oxygen electrode is further constituted by laminating a large number of sets of fuel cells (not shown) interposed between pairs of separators, for example.

The hydrogen is ionized over the catalytic electrode of the fuel electrode by the fuel gas, such as the hydrogen, supplied from the inlet side piping 6 to the fuel electrode and is moved to the oxygen electrode through the solid polymer electrolyte membrane which is properly humidified. An electron generated at that time is taken out into an external circuit and is utilized as a DC electrical energy. An oxidizing agent gas, such as oxygen or air, is supplied to the oxygen electrode through the inlet side piping 7. For this reason, a hydrogen ion, an electron and oxygen react so that water is produced at the oxygen electrode. Then, a so-called off-gas which has already been subjected to the reaction is discharged from the outlet side pipings 8 and 9 to the outside of a system at both the fuel electrode side and the oxygen electrode side.

Figure 2:
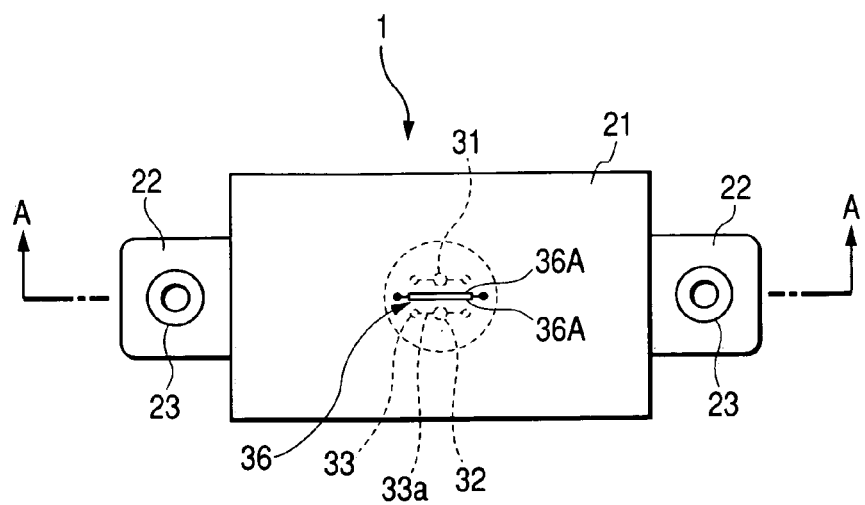
FIG. 2 is a sectional view showing the gas sensor illustrated in FIG. 1.
Figure 3:
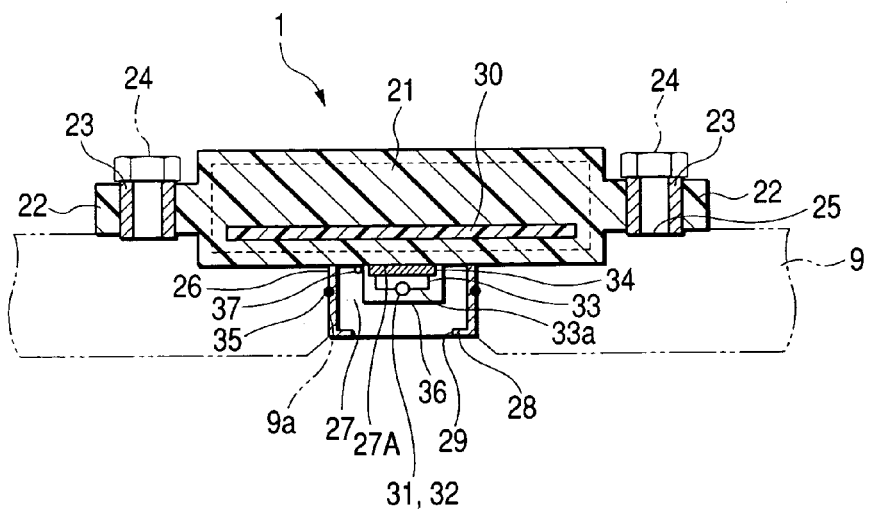
FIG. 3 is a schematic sectional view taken along an A—A line in FIG. 2.

For example, as shown in FIGS. 2 and 3, the gas sensor 1 comprises a case 21 taking the shape of a rectangular parallelepiped which is long in the longitudinal direction of the outlet side piping 9 extended in a horizontal direction, that is, the horizontal direction. The case 21 is formed of polyphenylenesulfide, for example, and includes a flange portion 22 on both ends in a longitudinal direction. A collar 23 is attached to the flange portion 22 and a bolt 24 is inserted into the collar 23 so that the flange portion 22 is fastened and fixed to a mounting seat 25 provided on the outlet side piping 9 at the oxygen electrode side as shown in FIG. 3, for example.

As shown in FIG. 3, for example, a cylindrical portion 26 is formed on the end face of the case 21 in the direction of a thickness, the inner part of the cylindrical portion 26 is formed as a gas detecting chamber 27, a flange portion 28 is inwardly formed on the inner side surface of the gas detecting chamber 27, and the inner peripheral portion of the flange portion 28 is opened as a gas introducing portion 29.

A circuit board 30 sealed with a resin is provided in the case 21 and a detecting unit 31 and a temperature compensating unit 32 which are provided in the cylindrical portion 26 are connected to the circuit board 30. The units 31 and 32 are provided to make a pair at a predetermined interval in a position placed apart by a predetermined distance in the direction of the thickness of the gas sensor 1 from a base 34 disposed on a bottom surface 27A of the gas detecting chamber 27 through a plurality of, for example, four stays 33 for current conductance and a lead wire 33*a* which are connected to the circuit board 30. Moreover, a seal member 35 is attached to the outer peripheral surface of the cylindrical portion 26 and is provided in close contact with the inner peripheral wall of a through hole 9*a* of the outlet side piping 9, thereby maintaining an airtightness.

Figure 4:
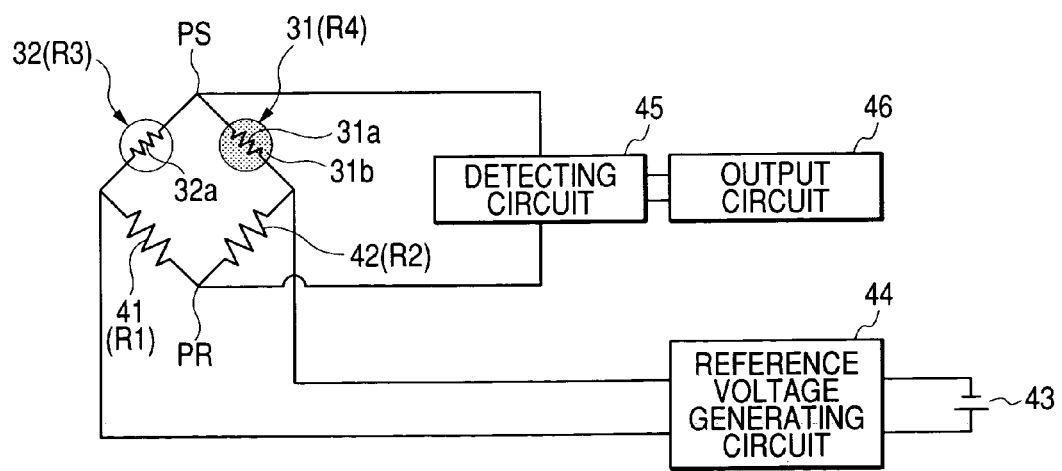
FIG. 4 is a circuit diagram showing the gas sensor illustrated in FIG. 1.

The detecting unit 31 is well known and the surface of a coil 31*a* of a metal wire, including platinum, having a high temperature coefficient to an electrical resistance is covered with a carrier, such as alumina, carrying a catalyst 31*b* formed of an active noble metal to hydrogen to be a detected gas as shown in FIG. 4, for example.

The temperature compensating unit 32 is inactive to the detected gas and the surface of a coil 32*a* which is equivalent to that of the detecting unit 31 is covered with a carrier, such as alumina, for example.

By utilizing the fact that a difference in an electrical resistance value is made between the detecting unit 31 having a temperature raised by the heat of a combusting reaction which is generated when the hydrogen to be the detected gas comes in contact with the catalyst 31*b* of the detecting unit 31 and the temperature compensating unit 32 having a lower temperature than the detecting unit 31 because of no generation of the combusting reaction by the detected gas, it is possible to offset a change in the electrical resistance value based on an atmospheric temperature, thereby detecting the concentration of the hydrogen.

For example, as shown in FIG. 2, a heater 36 taking the shape of an almost rectangular plate is provided in an erecting state in the direction of the flow of the detected gas in order to block both the detecting unit 31 and the temperature compensating unit 32 therebetween in the gas detecting chamber 27. The heater 36 is constituted by a resistor member and is electrified by the circuit board 30, thereby heating the inner part of the gas detecting chamber 27 and the units 31 and 32, and is provided with a radiating surface 36A directed toward the detecting unit 31 and the temperature compensating unit 32. In other words, each surface of the heater 36 is constituted as the radiating surface 36A. The detected gas flowing through the heater 36 is distributed evenly into the detecting unit 31 and the temperature compensating unit 32.

Moreover, a sensor 37 for detecting a temperature and a humidity in the gas detecting chamber 27 is attached to the gas detecting chamber 27.

For example, as shown in FIG. 4, in a bridge circuit in which a branch side having the detecting unit 31 (a resistance value R4) and the temperature compensating unit 32 (a resistance value R3) connected in series and a branch side having a fixed resistor 41 (a resistance value R1) and a fixed resistor 42 (a resistance value R2) connected in series are connected in parallel with a reference voltage generating circuit 44 for applying a predetermined reference voltage based on a voltage supplied from an external power supply 43, a detecting circuit 45 for detecting a voltage between a node PS of the detecting unit 31 and the temperature compensating unit 32 and a node PR of the fixed resistors 41 and 42 is connected between the Nodes PS and PR, and furthermore, an output circuit 46 is connected to the detecting circuit 45.

When the hydrogen to be the detected gas is not present in a gas to be inspected which is introduced into the gas detecting chamber 27, the bridge circuit is balanced in a state of R1×R4=R2×R3 and the output of the detecting circuit 45 becomes zero. On the other hand, when the hydrogen is present, it is combusted in the catalyst 31b of the detecting unit 31 and the temperature of the coil 31a is raised so that the resistance value R4 is increased. On the other hand, the hydrogen is not combusted in the temperature compensating unit 32 so that the resistance value R3 is not changed. Consequently, the balance of the bridge circuit is broken so that a proper voltage to be changed in a tendency of an increase corresponding to a change in the increase of the concentration of the hydrogen is applied to the detecting circuit 45. The detected value of the voltage output from the detecting circuit 45 is output to the output circuit 46, and the output circuit 46 outputs the input detected value to the control device 2. In the control device 2, the concentration of the hydrogen is calculated based on the map of the concentration of the hydrogen which is preset corresponding to a change in the detected value of the voltage.

The control device 2 is connected to the sensor 37 and the heater 36 in the gas detecting chamber 27, and controls the actuation states of the units 31 and 32 and the heater 36, for example, each of timings for starting and stopping current conductance and the amount of the current conductance depending on the state of a temperature or a humidity in the atmosphere in the gas detecting chamber 27 which is output from the sensor 37, and the load state and operation state of the fuel cell 5, for example. At this time, the control device 2 controls the amount of the current conductance to the heater 36 through a feedback control for the value of a current to be electrified to the heater 36 or a chopper control based on the ON/OFF operation of a switching unit (that is, the ON/OFF switching control of the current conductance), for example.

For example, the control device 2 controls the current conductance to the heater 36 based on a temperature detected by the sensor 37, and controls the timings for starting and stopping the current conductance to the heater 36 and the amount of the current conductance in such a manner that a temperature in the gas detecting chamber 27 which is detected from the sensor 37 is set within a predetermined temperature range which is higher than at least a dew-point temperature and a relative humidity in the gas detecting chamber 27 which is detected from the sensor 37 has the retrieved value of a relative humidity within a predetermined humidity range or a relative humidity obtained from the map of a relative humidity corresponding to a temperature condition in the gas detecting chamber 27 which is previously created, for example.

Furthermore, the control device 2 controls the amount of the current conductance to the heater 36 corresponding to the operation state of the fuel cell 5 (that is, an actuation state including the start and stop of the actuation of the fuel cell 5), a load state in the operation of the fuel cell 5, and the power generating state of the fuel cell 5 which is calculated based on a power generating command to be given to the fuel cell 5 (an FC output command value), the current value of the output current of the fuel cell 5 which is detected by an output current sensor (not shown), and the detected value of the flow of air supplied from an air compressor (not shown) to the fuel cell 5 which is detected by a flow sensor (not shown) in addition to the temperature state in the gas detecting chamber 27 which is detected by the sensor 37, for example.

For example, in the case in which the load state of the fuel cell 5 is changed into a high load state and there is a possibility that the flow of an off-gas flowing in the outlet side piping 9 on the oxygen electrode side might be increased to drop the temperature in the gas detecting chamber 27 of the gas sensor 1 exposed to the off-gas, and the amount of water produced in the fuel cell 5 and contained in the off-gas might be increased to increase the relative humidity in the gas detecting chamber 27, the control device 2 increases the amount of the current conductance to the heater 36 to raise the temperature in the gas detecting chamber 27, thereby preventing the generation of a dew condensation in the gas detecting chamber 27. On the other hand, in the case in which the load state of the fuel cell 5 is changed into a low load state, the control device 2 decreases the amount of the current conductance to the heater 36, thereby suppressing an excessive energy consumption.

In the case in which a purging process for increasing the flow of the off-gas fluidizing in each of the outlet side pipings 8 and 9 and discharging water remaining in a fuel cell system to an outside is executed when the actuation of the fuel cell 5 stops, for example, the control device 2 increases the amount of the current conductance to the heater 36 to temporarily raise the temperature in the gas detecting chamber 27, thereby increasing the amount of saturated vapor of an atmospheric gas in the gas detecting chamber 27 to prevent the generation of the dew condensation in the gas detecting chamber 27.

Moreover, the control device 2 starts to electrify the units 31 and 32 and the heater 36 in the gas sensor 1 prior to the start of the fluidization of the off-gas in the outlet side piping 9 on the oxygen electrode side when the actuation of the fuel cell 5 is started, and stops the fluidization of the off-gas in the outlet side piping 9 on the oxygen electrode side and then stops the current conductance to the units 31 and 32 and the heater 36 in the gas sensor 1 when the actuation of the fuel cell 5 stops.

The control device 2 gradually decreases the amount of current conductance to each of the units 31 and 32 (for example, an electrifying voltage) depending on a predetermined current conductance reducing amount which is preset or the state of a temperature or a humidity in the gas detecting chamber 27 which is detected by the sensor 37, thereby stopping the current conductance to each of the units 31 and 32 and gradually decreases the amount of current conductance to the heater 36, thereby stopping the current conductance to the heater 36 as will be described below.

Next, description will be given to the operation of the control device of the gas sensor according to the embodiment, particularly, a method of stopping the actuation of the gas sensor 1.

First of all, for example, when the ignition switch (IG) of a vehicle is turned OFF by a driver's operation, a purging process for increasing the flow of an off-gas fluidizing in each of the outlet side pipings 8 and 9 and discharging water remaining in a fuel cell system to an outside is started to be executed, and the amount of current conductance to the heater 36 is increased synchronously with the start of the execution of the purging process. With the completion of the purging process (a time t0 shown in FIG. 6), the fluidization of the off-gas in each of the outlet side pipings 8 and 9 stops to execute processings in and after a step S01 shown in FIG. 5.

Figure 5:
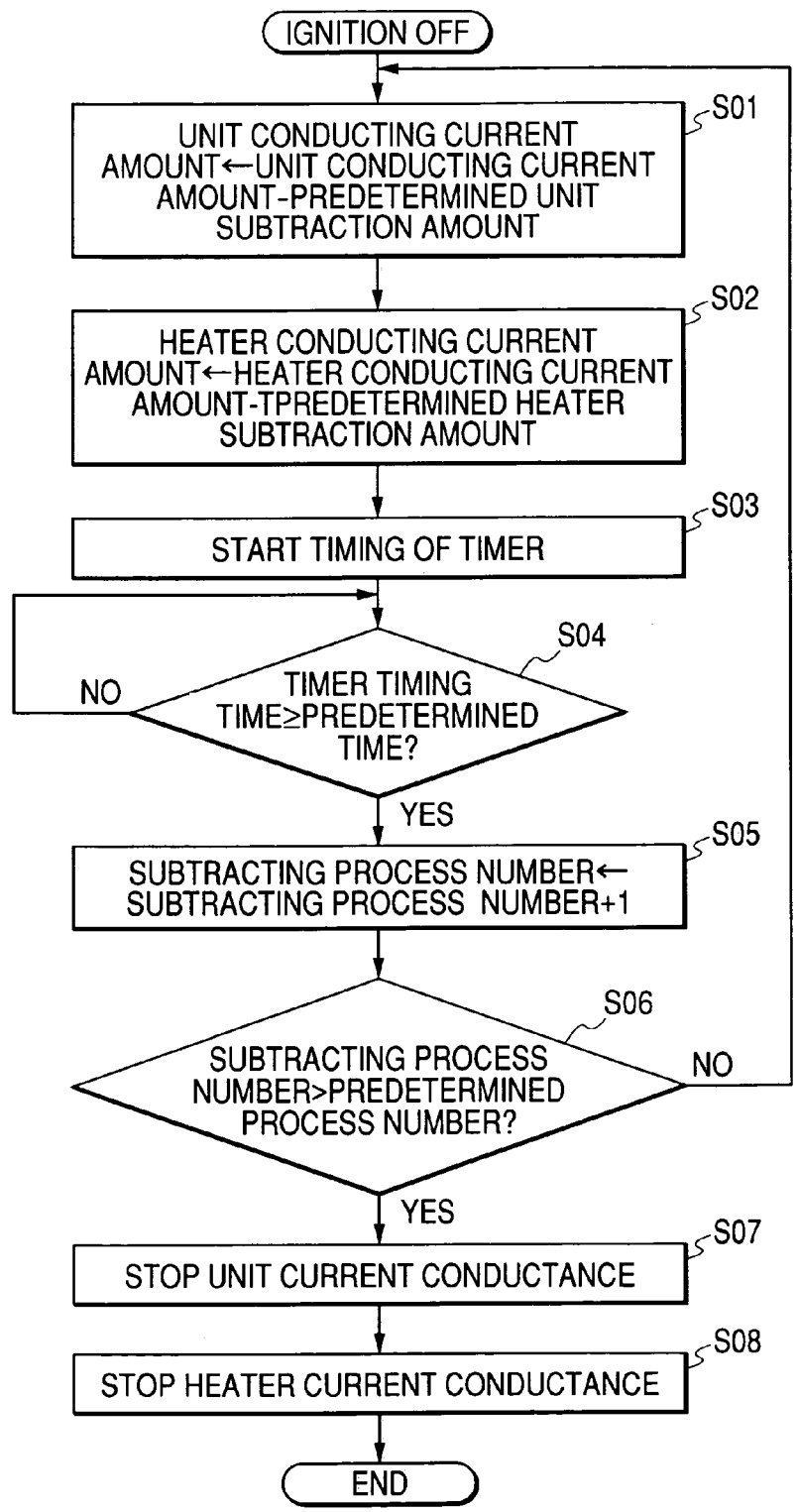
FIG. 5 is a flow chart showing the operation of the control device of the gas sensor illustrated in FIG. 1, particularly, a method of stopping the actuation of the gas sensor.
Figure 6:
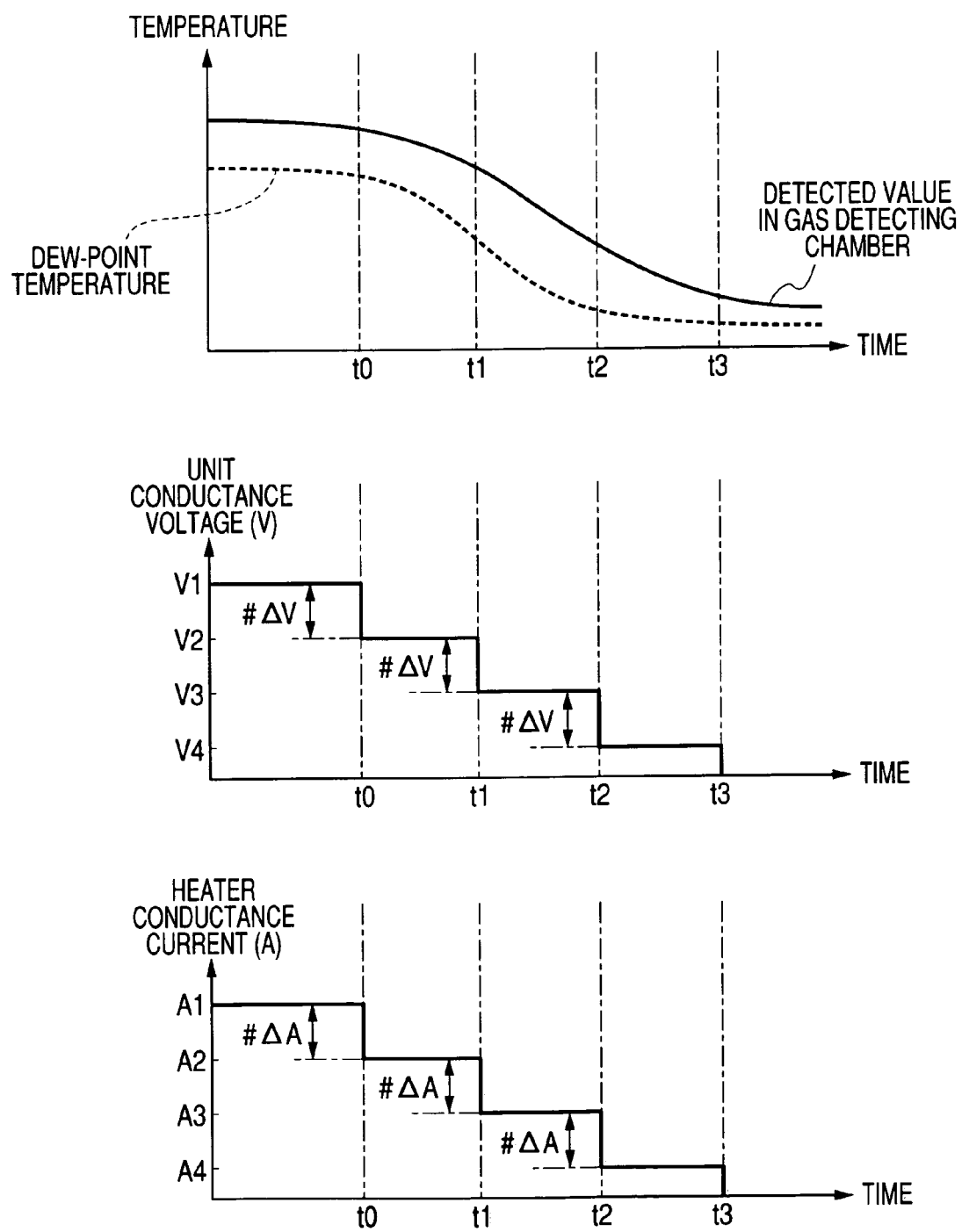
FIG. 6 is a graph showing an example of a temporal change in the amounts of current conductance to each of units and a heater in the gas sensor according to the embodiment illustrated in FIG. 1 and a temporal change in a temperature in a gas detecting chamber.

At the step S01 shown in FIG. 5, for example, a value obtained by subtracting a predetermined unit subtraction amount (for example, a predetermined subtraction voltage #ΔV shown in FIG. 6) from a unit current conductance amount for each of the units 31 and 32 (for example, an electrifying voltage) is newly set to be a unit current conductance amount.

At a step S02, then, a value obtained by subtracting a predetermined heater subtraction amount (for example, a predetermined subtraction current #ΔA shown in FIG. 6) from a heater current conductance amount for the heater 36 (for example, an electrifying current) is newly set to be a heater current conductance amount.

At a step S03, next, the timing of an current conductance continuing timer is started.

At a step S04, subsequently, it is decided whether or not the timer value of the current conductance continuing timer is equal to or greater than a predetermined current conductance time.

If the result of the decision is "NO", the processing of the step S04 is repeated.

On the other hand, if the result of the decision is "YES", the timer value of the current conductance continuing timer is reset and the processing proceeds to a step S05.

At the step S05, a value obtained by adding one to a subtraction processing number is newly set to be a subtraction processing number. The subtraction processing number is reset by turning OFF the ignition.

At a step S06, next, it is decided whether or not the subtraction processing number is greater than a predetermined processing number which is preset.

If the result of the decision at the step S06 is "NO", the processing returns to the step S01.

On the other hand, if the result of the decision at the step S06 is "YES", the processing proceeds to a step S07.

At the step S07, the unit current conductance amount is set to be zero to stop the current conductance to each of the units 31 and 32 at a time t3 shown in FIG. 6, for example.

At a step S08, subsequently, the heater current conductance amount is set to be zero to stop the current conductance to the heater 36 at the time t3 shown in FIG. 6, for example. Thus, a serial processing is carried out.

More specifically, according to the serial processing of the steps S01 to S08, such a value that the temperature of an atmospheric gas in the gas detecting chamber 27 (for example, a detected value in the gas detecting chamber shown in FIG. 6) and the temperature of the surface of each of the units 31 and 32 are higher than the dew-point temperature of the atmospheric gas (for example, a dew-point temperature shown in FIG. 6) is set to be a value obtained by a predetermined experiment or a simulation for each subtraction amount (that is, the predetermined subtraction voltage #ΔV and the predetermined subtraction current #ΔA) in a decrease in the current conductance amount for each of the units 31 and 32 and the amount of current conductance for the heater 36 and a predetermined time required for continuing the current conductance in each current conductance amount.

As compared with the case in which the unit current conductance amount and the heater current conductance amount are instantly set to be zero stepwise, for example, when the actuation of the gas sensor 1 stops, consequently, it is possible to prevent the temperature of the atmospheric gas in the gas detecting chamber 27 and the temperature of the surface of each of the units 31 and 32 from being suddenly dropped to be equal to or lower than the dew-point temperature of the atmospheric gas in the gas detecting chamber 27, thereby suppressing the generation of a dew condensation in the gas detecting chamber 27.

As described above, according to the control device of the gas sensor in accordance with the embodiment, as compared with the case in which the unit current conductance amount and the heater current conductance amount are instantly set to be zero, for example, when the actuation of the gas sensor 1 stops, it is possible to prevent the temperature of the atmospheric gas in the gas detecting chamber 27 and the temperature of the surface of each of the units 31 and 32 from being suddenly dropped to be equal to or lower than the dew-point temperature of the atmospheric gas in the gas detecting chamber 27, thereby suppressing the generation of a dew condensation in the gas detecting chamber 27.

Figure 7:
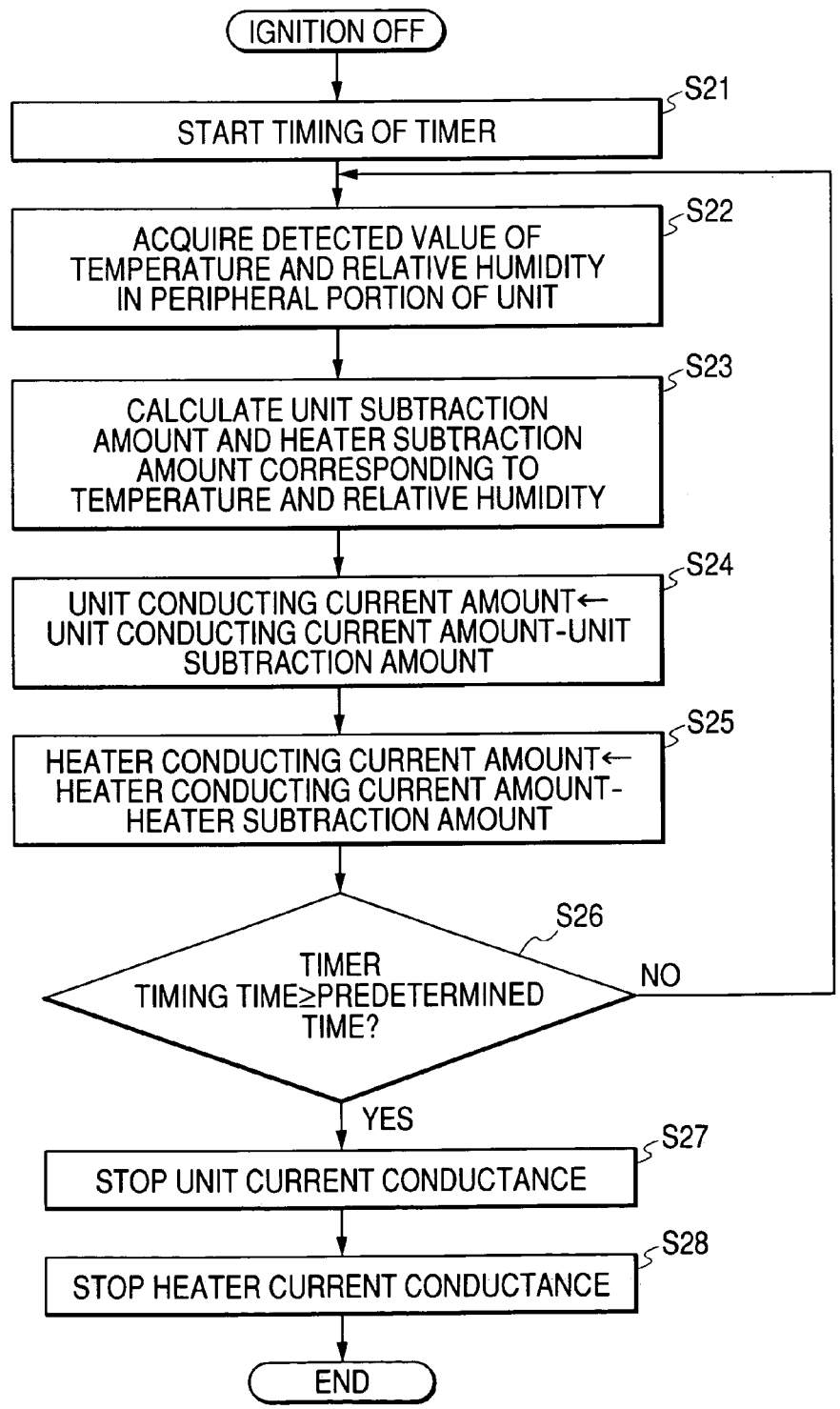
FIG. 7 is a flow chart showing the operation of the control device of a gas sensor according to a first variant of the embodiment illustrated in FIG. 1, particularly, a method of stopping the actuation of the gas sensor.

While the current conductance amount for each of the units 31 and 32 and the heater 36 is gradually decreased depending on each preset subtraction amount (that is, the predetermined subtraction voltage #ΔV and the predetermined subtraction current #ΔA) in the embodiment, this is not restricted but it is also possible to set each subtraction amount (that is, the predetermined subtraction voltage #ΔV and the predetermined subtraction current #ΔA) depending on the state of a temperature or a humidity in the gas detecting chamber 27 which is detected by the sensor 37 as in the method of stopping the actuation of the gas sensor 1 according to a variant of the embodiment shown in FIG. 7, for example, or to set a predetermined time required for continuing the current conductance in each current conductance amount depending on the state of the temperature or the humidity in the gas detecting chamber 27 in addition to each subtraction amount (that is, the predetermined subtraction voltage #ΔV and the predetermined subtraction current #ΔA).

For example, at a step S21 shown in FIG. 7, the timing of a subtracting process continuing timer is started.

At a step S22, next, the detected values of a temperature and a relative humidity in the gas detecting chamber 27 which are detected by the sensor 37 are acquired.

Figure 8:
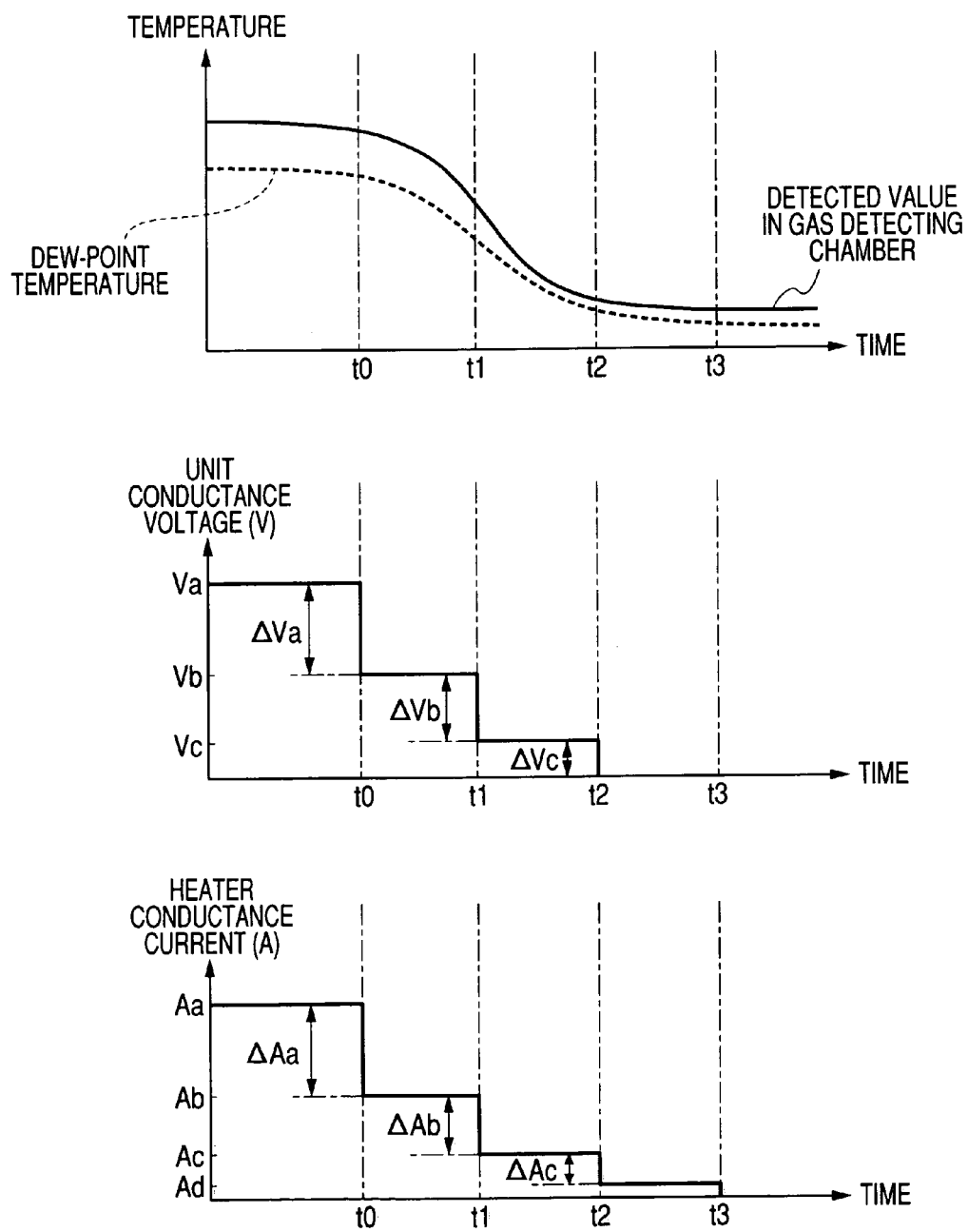
FIG. 8 is a graph showing an example of a temporal change in the amounts of current conductance to each of units and a heater in the gas sensor according to the first variant of the embodiment illustrated in FIG. 1 and a temporal change in a temperature in a gas detecting chamber.

At a step S23, then, a unit subtraction amount (for example, subtraction voltages ΔVa, ΔVb and ΔVc shown in FIG. 8) and a heater subtraction amount (for example, subtraction currents ΔAa, ΔAb and ΔAc shown in FIG. 8) are calculated according to the detected values of the temperature and the relative humidity in the gas detecting chamber 27 which are acquired in such a manner that the surface temperature of each of the units 31 and 32 and the temperature of the atmospheric gas in the gas detecting chamber 27 (for example, a detected value in the gas detecting chamber shown in FIG. 8) are higher than the dew-point temperature of the atmospheric gas (for example, a dew-point temperature shown in FIG. 8).

At a step S24, thereafter, a value obtained by subtracting the unit subtraction amount from the unit current conductance amount for each of the units 31 and 32 is newly set to be a unit current conductance amount.

At a step S25, subsequently, a value obtained by subtracting the heater subtraction amount from the heater current conductance amount for the heater 36 is newly set to be a heater current conductance amount.

At a step S26, next, it is decided whether or not the timer value of the subtracting process continuing timer is equal to or greater than a predetermined time.

If the result of the decision is "NO", the processing returns to the step S22.

On the other hand, if the result of the decision is "YES", the timer value of the subtracting process continuing timer is reset and the processing proceeds to a step S27.

At the step S27, the unit current conductance amount is set to be zero to stop the current conductance to each of the units 31 and 32 at a time t3 shown in FIG. 8, for example.

At a step S28, subsequently, the heater current conductance amount is set to be zero to stop the current conductance to the heater 36 at the time t3 shown in FIG. 8, for example. Thus, a serial processing is carried out.

More specifically, according to the serial processing of the steps S21 to S28, each subtraction amount (that is, the subtraction voltages ΔVa, ΔVb and ΔVc and the subtraction currents ΔAa, ΔAb and ΔAc) in a decrease in the amount of current conductance to each of the units 31 and 32 and the amount of current conductance to the heater 36 are set to have such values that the temperature of the atmospheric gas in the gas detecting chamber 27 (for example, a detected value in the gas detecting chamber shown in FIG. 8) is higher than the dew-point temperature (for example, a dew-point temperature shown in FIG. 8) through a feedback control corresponding to the detected values of the temperature and the relative humidity in the gas detecting chamber 27 which are detected by the sensor 37.

As compared with the case in which the unit current conductance amount and the heater current conductance amount are instantly set to be zero, for example, when the actuation of the gas sensor 1 stops, consequently, it is possible to prevent the temperature of the atmospheric gas in the gas detecting chamber 27 and the temperature of the surface of each of the units 31 and 32 from being suddenly dropped to be equal to or lower than the dew-point temperature of the atmospheric gas in the gas detecting chamber 27, thereby suppressing the generation of a dew condensation in the gas detecting chamber 27. In addition, as compared with the case in which the amounts of current conductance to each of the units 31 and 32 and the heater 36 are gradually decreased depending on each of the preset subtraction amounts, it is possible to shorten a time required for continuing the current conductance to each of the units 31 and 32 and the heater 36, thereby reducing a power consumption still more.

While the gas sensor 1 is set to be the hydrogen sensor in the embodiment, this is not restricted but a gas sensor for detecting another gas, for example, a flammable gas, such as carbon monoxide or methane, may be used.

Although the bridge circuit is used for connecting the units 31 and 32 to each other in the embodiment, moreover, this is not restricted, but another circuit, such as a series circuit, may be used and the detected value of a voltage or a current between predetermined contacts may be output, to the control device 2, as a state amount related to the resistance value R4 of the detecting unit 31.

While the heater 36 is provided between the detecting unit 31 and the temperature compensating unit 32 in the embodiment, furthemore, this is not restricted, but the heater 36 may be provided in a shifted position toward the unit 31 and 32 sides from a position in which a dehumidifying member (not shown), is disposed between each of the units 31 and 32 and the gas introducing portion 29 in the gas detecting chamber 27, for example.

It will be apparent to those skilled in the art that various modifications and variations can be made to the described preferred embodiments of the present invention without departing from the spirit or scope of the invention. Thus, it is intended that the present invention cover all modifications and variations of this invention consistent with the scope of the appended claims and their equivalents.

The invention claimed is:

1. A control device of a gas sensor for detecting a concentration of a detected gas contained in a gas to be inspected based on a difference in an electrical resistance value between a detecting unit and a compensating unit, comprising:
    a signal input port operational to received a detected signal output from the gas sensor;
    current conductance reducing amount setting means for setting a predetermined current conductance reducing amount when stopping the gas sensor; and
    unit current conductance stopping means for gradually decreasing amounts of current conductance to the detecting unit and the compensating unit, depending on the predetermined current conductance reducing amount set by the current conductance reducing amount setting means.

2. The control device of a gas sensor according to claim 1, wherein the detecting unit and the compensating unit are provided in a gas detecting chamber for introducing the gas to be inspected, the control device further comprising:
    a heater provided in the gas detecting chamber; and
    heater current conductance stopping means for gradually decreasing an amount of current conductance to the heater.

3. The control device of a gas sensor according to claim 2, further comprising state detecting means for detecting a humidity state of an atmosphere in the gas detecting chamber, the heater current conductance stopping means decreasing the amount of current conductance to the heater depending on the humidity state of the atmosphere in the gas detecting chamber which is detected by the state detecting means.

4. The control device of a gas sensor according to claim 2, wherein the heater current conductance stopping means sets the amount of current conductance to the heater in such a manner that surface temperatures of the detecting unit and the compensating unit are higher than a dew-point temperature of an atmosphere in the gas detecting chamber.

5. The control device of a gas sensor according to claim 2, further comprising temperature detecting means for detecting a temperature in the gas detecting chamber, the heater current conductance stopping means decreasing the amount of current conductance to the heater depending on the temperature detected by the temperature detecting means.

6. The control device of a gas sensor according to claim 1, wherein the detecting unit and the compensating unit are provided in a gas detecting chamber for introducing the gas to be inspected, the control device further comprising:

state detecting means for detecting a humidity state of an atmosphere in the gas detecting chamber, the unit current conductance stopping means decreasing the amounts of current conductance to the detecting unit and the compensating unit in accordance with the humidity state of the atmosphere in the gas detecting chamber which is detected by the state detecting means.

7. The control device of a gas sensor according to claim 1, wherein the detecting unit and the compensating unit are provided in a gas detecting chamber for introducing the gas to be inspected, and the unit current conductance stopping means sets the amounts of current conductance to the detecting unit and the compensating unit in such a manner that surface temperatures of the detecting unit and the compensating unit are higher than a dew-point temperature of an atmosphere in the gas detecting chamber.

8. The control device of a gas sensor according to claim 1, wherein the detecting unit and the compensating unit are provided in a gas detecting chamber for introducing the gas to be inspected, the control device further comprising:

temperature detecting means for detecting a temperature in the gas detecting chamber, the current conductance reducing amount setting means setting the predetermined current conductance reducing amount depending on the temperature detected by the temperature detecting means.

* * * * *

UNITED STATES PATENT AND TRADEMARK OFFICE
CERTIFICATE OF CORRECTION

| | | |
|---|---|---|
| PATENT NO. | : 7,096,717 B2 | Page 1 of 1 |
| APPLICATION NO. | : 10/938297 | |
| DATED | : August 29, 2006 | |
| INVENTOR(S) | : Oishi et al. | |

It is certified that error appears in the above-identified patent and that said Letters Patent is hereby corrected as shown below:

Title Page, column 2 under item [56] References Cited --Foreign Application Priority Data: September 19, 2003    (JP)   ….…...2003-328924-- should be included Signed and Sealed this Sixth Day of March, 2007

JON W. DUDAS
*Director of the United States Patent and Trademark Office*